United States Patent [19]
Plath et al.

[11] Patent Number: 4,832,731
[45] Date of Patent: May 23, 1989

[54] QUINOLINE-8-CARBOXYLIC ACID AZOLIDES AND THEIR USE AS HERBICIDES

[75] Inventors: Peter Plath, Frankenthal; Karl Eicken, Wachenheim; Helmut Hagen, Frankenthal; Rolf-Dieter Kohler, Edingen-Neckarhausen; Juergen Markert, Mutterstadt; Norbert Meyer, Ladenburg; Bruno Wuerzer, Otterstadt, all of Fed. Rep. of Germany

[73] Assignee: BASF Aktiengesellschaft, Ludwigshafen, Fed. Rep. of Germany

[21] Appl. No.: 883,815

[22] Filed: Jul. 9, 1986

[30] Foreign Application Priority Data
Jul. 12, 1985 [DE] Fed. Rep. of Germany ....... 3524918

[51] Int. Cl.⁴ .................... C07D 403/02; A01N 43/42
[52] U.S. Cl. ........................................... 71/92; 71/94; 546/168; 546/169
[58] Field of Search .................... 546/168, 169; 71/94, 71/92

[56] References Cited

U.S. PATENT DOCUMENTS

| | | | |
|---|---|---|---|
| 3,277,171 | 10/1966 | Hopkins et al. | 71/92 |
| 4,147,694 | 4/1979 | Erickson | 546/169 |
| 4,497,651 | 2/1985 | Hagen et al. | 71/94 |

FOREIGN PATENT DOCUMENTS

| | | | |
|---|---|---|---|
| 0060429 | 2/1982 | Fed. Rep. of Germany . | |
| 3108873 | 9/1982 | Fed. Rep. of Germany . | |
| 2092131 | 12/1980 | United Kingdom | 71/95 |

*Primary Examiner*—David B. Springer
*Attorney, Agent, or Firm*—Keil & Weinkauf

[57] ABSTRACT

Quinoline-8-carboxylic acid azolides of the formula

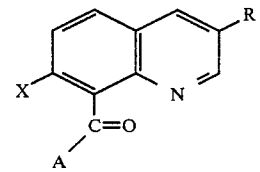

where A, X and R have the meanings given in the disclosure, and their use as herbicides.

12 Claims, No Drawings

QUINOLINE-8-CARBOXYLIC ACID AZOLIDES AND THEIR USE AS HERBICIDES

The present invention relates to novel quinoline-8-carboxylic acid azolides, herbicides which contain these compounds, and a method for controlling undesirable plant growth.

Herbicides based on quinoline-8-carboxylic acid are disclosed in EP-A-60 429.

We have found novel quinoline-8-carboxylic acid azolides of the formula I

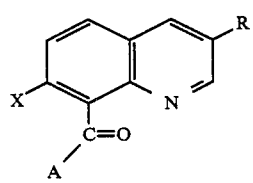

where R is hydrogen, halogen, $C_1$—$C_4$—alkyl, $C_1$—$C_4$—haloalkyl, formyl or cyano, X is halogen and A is a five-membered heterocyclic structure which contains two or three nitrogen atoms in the ring, is bonded to the carbonyl group via a nitrogen atom and may be unsubstituted or monosubstituted or polysubstituted by halogen, $C_1$—$C_4$—alkyl, $C_1$—$C_4$—alkoxycarbonyl, cyano, trifluoromethyl, mercapto, methylthio, methylsulfonyl, methoxy, amino or nitro, and, when the heterocyclic structure is 1,2,3-triazole or imidazole which is unsubstituted or substituted in the 2-position by methyl or trifluoromethyl, may furthermore be benzofused.

The novel azolides have good herbicidal action and are well tolerated by certain crops. They also have advantageous properties with regard to mobility in the soil.

In formula I, R is, for example, hydrogen, fluorine, chlorine, bromine, methyl, ethyl, n-propyl, isopropyl, sec-butyl or isobutyl, preferably chlorine or methyl, X may be, for example, fluorine, chlorine or bromine, but is preferably chlorine, and A is, for example, unsubstituted pyrazole or pyrazole which is monosubstituted, disubstituted or trisubstituted, such as 4-chloropyrazole, 4-nitropyrazole, 3,5-dimethylpyrazole, 3-methyl-5-chloropyrazole, 3,5-dimethyl-4-chloropyrazole, 3,5-dimethyl-4-bromopyrazole, 3,5-dimethyl-4-nitropyrazole 3-trifluoromethylpyrazole, 3-trifluoromethyl-5-chloropyrazole, 3,5-bistrifluoromethylpyrazole, 4-methoxycarbonylpyrazole or 4-cyanopyrazole.

A is furthermore, for example, unsubstituted imidazole, imidazole which is monosubstituted, disubstituted or trisubstituted, such as 4-chloroimidazole, 2,4-dichloroimidazole, 4,5-dichloroimidazole, 4-nitroimidazole, 4-nitro-5-chloroimidazole, 4-nitro-5-methylthioimidazole or 4-nitro-5-methlsulfonylimidazole, benzimidazole or monosubstituted benzimidazole, such as 2-trifluoromethylbenzimidazole or 2-methlbenzimidazole, unsubstituted triazole, eg. 1,2,4-triazole or 1,2,3-triazole, or triazole which is monosubstituted or disubstituted, eg. 5-chloro-1,2,4-triazole, 3(5)-methyl-1,2,4-triazole, 3,5-dimethyl-1,2,4-triazole, 3-methyl-5-chloro-1,2,4-triazole, 3,5-dichloro-1,2,4-triazole, 3,5-bistrifluoromethyl-1,2,4-triazole, 5-amino-3-n-butyl-1,2,4-triazole, 5-mercapto-1,2,4-triazole, 5-methoxy-1,2,4-triazole or 5-methylthio-1,2,4-triazole, or 1,2,3-benzotriazole.

Preferred azoles are 1,2,4-triazole, imidazole, 5-mercapto-1,2,4-triazole and 5-amino-1,2,4-triazole.

The novel quinoline-8-carboxylic acid azolides are obtained by reacting an acyl chloride of the formula II

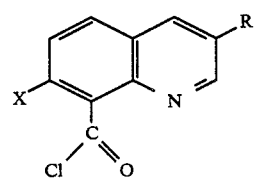

with an axole of the formula A-H, where R, X and A each have the above meanings. The acyl chloride may also be used in the form of its hydrochloride.

Because azoles of the formula A-H occur in tautomeric forms (eg. 4-chloro-1H-imidazole and 4-chloro-3H-imidazole, isomeric azolides may be formed in the reaction.

The reaction of the quinoline-8-carboxylic acid chlorides with the azoles is carried out in the presence of a base and of an inert solvent at from 0° to 100° C., preferably from 20° to 60° C.

From 2 to 10 moles of base are added permole of acyl chloride. Suitable bases are tertiary amines, such as triethylamine, tri-n-propylamine, N,N-dimethylcyclohexylamine, N-methylpiperidine and pyridine, triethylamine being preferably used.

Examples of suitable inert solvents are methylene chloride, 1,1,1-trichloroethane, tetrahydrofuran, dioxane, ethyl acetate, toluene and chlorobenzene, methylene chloride or 1,1,1-trichloroethane being preferably used.

In the preparation of the compounds I, it is advantageous if the acyl chloride is initially taken together with the inert solvent and the base. The particular azole is then added at from 0° to 30° C., and the mixture is stirred for from 5 to 16 hours at from 20° to 100° C. The resulting azolide, which in general is sparingly soluble, is then filtered off under suction, washed with water and dried.

The quinoline-8-carboxylic acid chlorides required for the reaction are obtained by reacting the corresponding free quinoline-8-carboxylic acid with thionyl chloride in a conventional manner in an inert solvent (eg. toluene, xylene or chlorobenzene) at from 30° to 120° C. Advantageously, from 1.2 to 20 moles of thionyl chloride are used per mole of free acid. When the reaction is complete, which is generally the case after 3–12 hours, the acyl chloride is filtered off under suction, washed and dried.

The particular quinoline-8-carboxylic acid chlorides are obtained either in free form or as the hydrochloride. However, this is not important for the subsequent azolide formation since, as stated above, either the free acyl chloride or its hydrochloride may be employed in this stage.

The appropriate free quinoline-8-carboxylic acids used in the reaction are described in DE-A-3 108 873.

The Examples which follow illustrate the invention.

EXAMPLE 1

3,7-Dichloroguinoline-8-carboxylic acid chloride 242 g (1 mole) of 3,7-dichloroquinoline-8-carboxylic acid were suspended in 1 l of toluene, 3 ml of dimethylformamide were added, and the mixture was heated to 60° C. Thereafter, 238 g (2 moles) of thionyl chloride were added dropwise at a rate such that a temperature of 60°–70° C. could be maintained. The mixture was then heated at the boil until evolution of gas (HCL, $SO_2$) could no longer be observed.

The major part of the desired product was precipitated on cooling. It was isolated by filtration under suction and was washed with diethyl ether. The toluene and unconsumed thionyl chloride were stripped off from the filtrate, and the residue was triturated with diethyl ether to give additional product. 246 g (94% of theory) of a colorless solid of melting point 120°–122° C. were obtained.

EXAMPLE 2

1,2,4-triazolide of 3,7-dichloroquinoline-8-carboxylic acid 296.5 g (1.1 mole) of the acyl chloride prepared in Example 1, in a mixture of 2.5 l of methylene chloride and 499 g (4.8 moles) of triethylamine, were initially taken. Thereafter, 111 g (1.6 moles) of 1,2,4-triazole were added a little at a time at from 20° to 30° C., and the mixture was stirred for 16 hours at 25° C. The desired product was obtained in the form of a sparingly soluble colorless solid, in addition to triethylamine hydrochloride. The mixture of solids was freed from methylene chloride by filtration under suction, added to 2 l of water, stirred for a short time, filtered off under suction again, washed with water and then dried at 50° C. under reduced-pressure. 245 g (76% of theory) of a colorless solid of melting point 261°–263° C. (Compound No. 1) were obtained.

The compounds listed in Table 1 were prepared similarly to Example 2 (for definitions of the radicals, see formula I; X is chlorine).

(As stated above, the occurrence of tautomeric forms in the case of the azoles may result in the formation of isomeric azolides. For this reason, the position of bonding to the azole ring has not been specified.)

TABLE 1

| Compound No. | R | A | Mp. °C. |
| --- | --- | --- | --- |
| 2 | Cl | Pyrazolyl | 213–215 |
| 3 | Cl | 4-Chloropyrazolyl | 214–215 |
| 4 | Cl | Imidazolyl | 184–186 |
| 5 | Cl | 5-Nitroimidazolyl | 245 |
| 6 | Cl | Benzimidazolyl | 144–146 |
| 7 | Cl | 3,5-Dimethyl-1,2,4-triazolyl | 210–212 |
| 8 | Cl | 3(5)-Chloro-1,2,4-triazolyl | 200–201 |
| 9 | Cl | 3(5)-Amino-1,2,4-triazolyl | 248–249 |
| 10 | Cl | 3(5)-Mercapto-1,2,4-triazolyl | 120 (decomposition) |
| 11 | Cl | 5(3)-Methylthio-3(5)-amino-1,2,4-triazolyl | 284–285 |
| 12 | Cl | 5(3)-n-Butyl-3(5)-amino-1,2,4-triazolyl | 285–286 |
| 13 | Cl | 1,2,3-Benzotriazolyl | 225–227 |
| 14 | $CH_3$ | Pyrazolyl | 206–208 |
| 15 | $CH_3$ | Imidazolyl | 164–166 |
| 16 | $CH_3$ | 4,5-Dichloroimidazolyl | 160–162 |
| 17 | $CH_3$ | Benzimidazolyl | 142–144 |
| 18 | $CH_3$ | 1,2,4-Triazolyl | 233–235 |
| 19 | $CH_3$ | 3(5)-Mercapto-1,2,4-triazolyl | 300 (decomposition) |
| 20 | $CH_3$ | 3(5)-Amino-1,2,4-triazolyl | 300 |
| 21 | $CH_3$ | Benzotriazolyl | 139–141 |

Other novel compounds of the formula I are the substances stated in Table 2:

TABLE 2

| R | X | A | R | X | A |
| --- | --- | --- | --- | --- | --- |
| H | Cl | 1,2,4-Triazolyl | Cl | Cl | 2,4-Dichloroimidazolyl |
| Br | Cl | 1,2,4-Triazolyl | Cl | Cl | 4,5-Dichloroimidazolyl |
| $C_2H_5$ | Cl | 1,2,4-Triazolyl | $CH_3$ | Cl | 4-Nitroimidazolyl |
| i-$C_3H_7$ | Cl | 1,2,4-Triazolyl | $CH_3$ | Cl | 4-Nitro-5-chloroimidazolyl |
| sec-$C_4H_9$ | Cl | 1,2,4-Triazolyl | Cl | Cl | 4-Nitro-5-S—$CH_3$—imidazolyl |
| $CF_3$ | Cl | 1,2,4-Triazolyl | Cl | Cl | 4-$NO_2$—5-$SO_2CH_3$—imidazolyl |
| Cl | Cl | 4-Nitropyrazolyl | Cl | Cl | 2-$CF_3$—benzimidazolyl |
| Cl | Cl | 3,5-Dimethyl-pyrazolyl | Cl | Cl | 2-$CH_3$—benzimidazolyl |
| Cl | Cl | 3-Methyl-5-chloro pyrazolyl | $CH_3$ | Cl | 1,2,3-Triazolyl |
| Cl | Cl | 3,5-Dimethyl-4-chloropyrazolyl | Cl | Cl | 1,2,3-Triazolyl |
| Cl | Cl | 3,5-Dimethyl-4-$NO_2$—pyrazolyl | $CH_3$ | Cl | 5-Chloro-1,2,4-triazolyl |
| $CH_3$ | Cl | 3-Trifluoromethyl-pyrazolyl | $CH_3$ | Cl | 3,5-Dimethyl-1,2,4-triazolyl |
| $CH_3$ | Cl | 3-$CF_3$—5-Cl—pyrazolyl | Cl | Cl | 3-Methyl-5-Cl-1,2,4-triazolyl |
| $CH_3$ | Cl | 3,5-$(CF_3)_2$—pyrazolyl | $CH_3$ | Cl | 3,5-$Cl_2$—1,2,4-triazolyl |
| Cl | Cl | 4-$CO_2$—$CH_3$—pyrazolyl | Cl | Cl | 3,5-$(CF_3)_2$—1,2,4-triazolyl |
| Cl | Cl | 4 CN—Pyrazolyl | Cl | Cl | 5-$NH_2$—3-$CH_3$—1,2,4-triazolyl |
| Cl | Cl | 4-Chloroimidazolyl | Cl | Cl | 5-$SCH_3$—1,2,4-triazolyl |
| Cl | F | 1,2,4-Triazolyl | Cl | Cl | 5-$OCH_3$—1,2,4-triazolyl |
| Cl | Br | 1,2,4-Triazolyl | | | |

The azolides according to the invention possess surprising stability to water and alcohols. For example, the imidazolide (Compound No. 4) can be recrystallized from methanol without the corresponding methyl quinoline-8-carboxylate being formed.

The resistance to hydrolysis is demonstrated by the Example below.

EXAMPLE 3

0.1 g of 3,7-dichloroguinoline-8-carboxylic acid triazolide (Compound No. 1) was mixed with 85 g of loamy sand and 100 ml of water and stirred for 14 days at 25° C. Every 3 days, a sample was taken and examined by thin layer chromatography. Compound No. 1 was found to be unchanged, and the corresponding free acid was not detected.

The compounds of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, buty they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 9 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 15 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 19 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 4 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oil dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combatted and their growth stage, and varies from 0.1 to 5kg/ha and more. The action and selectively of the compounds are demonstrated below with reference to some of the novel active ingredients.

The action of the quinoline-8-carboxylic acid azolides on plant growth is demonstrated in greenhouse experiments.

The vessels employed were plastic flowerpots having a volume of 300 cm$^3$, and which were filled with a sandy loam containing about 3.0% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rates were 1.0 and 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplanted to the pots a few days before treatment. The application rates for postemergence treatment were 0.5, 1.0 and 3.0 kg of active ingredient per hectare.

The following test plants were used in the experiments: Avena sativa, Beta vulgaris, Echinochloa crusgalli, Galium aparine, Lolium multiflorum, Oryza sativa, Sesbania exaltata, Sinapis alba, Triticum aestivum and Veronica spp.

The pots were set up in the greenhouse - species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

On preemergence application of 3.0 kg/ha, for instance compound no. 9 has a considerable herbicidal action on representatives of broadleaved and grassy plants. Echinochloa crus-galli is well combatted with compounds nos. 1 and 9 selected by way of example, while the crop plant rice suffers minor damage at most.

For example compounds nos. 9, 4 and 1 illustrate the effectiveness of the novel compounds on postemergence application - grassy and broadleaved plants are combatted well with 3.0 kg/ha.

For instance compounds nos. 15, 9 and 2 at a rate of 3 kg/ha, and compounds nos. 15 and 19 at a rate of 1.0 kg/ha may be used postemergence to combat unwanted broadleaved plants in cereals. The damage to oats and wheat is negligible.

Compounds nos. 15 and 19 may also be used for combatting important weeds in sugar beets.

For example compound no. 1 is also suitable, when applied postemergence at a rate of 0.5 kg/ha, for combatting unwanted broadleaved vegetation in rice.

In view of the fact that the herbicides according to the invention are well tolerated by numerous broadleaved and other crops and can be applied by a variety of methods, they—or agents containing them—can be used in a further large number of crops for removing unwanted plant growth.

The following crops may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum | parsley |

| Botanical name | Common name |
| --- | --- |
| spp. *tuberosum* | |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor (s. vulgare)* | sorghum |
| *Sorghum dochna* | sorgo |
| *Spinacia oleracea* | spinach |
| *Theobroma cacao* | cacao plants |
| *Trifolium pratense* | red clover |
| *Vaccinium corymbosum* | blueberries |
| *Vaccinium vitis-idaea* | cranberries |
| *Vicia faba* | tick beans |
| *Vigna sinensis (V. unguiculata)* | cow peas |
| *Vitis vinifera* | grapes |
| *Zea mays* | Indian corn, sweet corn, maize (post-directed) |

To increase the spectrum of action and to achieve synergistic effects, the novel compounds may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the the compounds, either alone or in combination with other herbicides, in admixture with other crop protection agents, e.g., agents for combatting pests or phytopathogenic fungi or bacteria. The compounds may also be mixed with solutions of mineral salts used to remedy nutritional or trace element deficiencies.

We claim:

1. A quinoline-8-carboxylic acid axolide of the formula

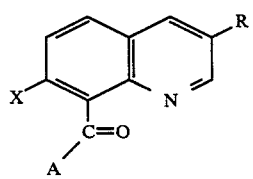

(I)

where R is hydrogen, halogen, $C_1$—$C_4$—alkyl or $C_1$—$C_4$— haloalkyl, X is halogn and A is a five-membered heterocyclic structure which contains two or three nitrogen atoms in the ring, is bonded to the carbonyl group via a nitrogen atom and may be unsubstituted or monosubstituted by chlorine, methyl cyano, trifluoromethyl, mercapto, methylthio, methylsulfonyl, methoxy, amino or nitro.

2. A quinoline-8-carboxylic acid azolide of the formula I as set forth in claim 1, where R is halogen or $C_1$—$C_4$—alkyl, X is fluorine, chlorine or bromine, and A is unsubstituted pyrazole, imidazole, benzimidazole or triazole; mono-, di- or trisubstituted pyrazole or imidazole; mono- or disubstituted triazole; or monosubstituted benzimidazole, which substituted radicals bear chlorine, nitro, methyl, trifluoromethyl, methoxy, cyano or methylsulfonyl as substituents.

3. A quinoline-8-carboxylic acid azolide of the formula I as set forth in claim 1, where R is chlorine or methyl, X is chlorine and A is unsubstituted pyrazole, imidazole, benzimidazole or triazole; mono-, di- or trisubstituted pyrazole or imidazole; mono- or disubstituted triazole; or monosubstituted benzimidazole, which substituted radicals bear chlorine, nitro, methyl, trifluoromethyl, methoxy, cyano or methylsulfonyl as substituents.

4. A quinoline-8-carboxylic acid azolide of the formula I as set forth in claim 1, where R is chlorine or methyl, X is chlorine and A is 1,2,4-triazole, imidazole, 5-mercapto-1,2,4-triazole or 5-amino-1,2,4-triazole.

5. A herbicidal composition containing a herbicidally effecitive amount of a quinoline-8-carboxylic acid azolide of the formula I as set forth in claim 1, and at least one carrier.

6. A herbicidal composition containing a herbicidally effective amount of a quinoline-8-carboxylic acid azolide of the formula I as set forth in claim 2, and at least one carrier.

7. A herbicidal composition containing a herbicidally effective amount of a quinoline-8-carboxylic acid azolide of the formula I as set forth in claim 3, and at least one carrier 8. A herbicidal composition containing a herbicidally effective amount of a quinoline-8-carboxylic acid azolide of the formula I as set forth in claim 4, and at least one carrier.

9. A process for combatting the growth of unwanted plants, wherein the plants and/or the area to be kept free from unwanted plant growth are treated with a herbicidally effective amount of a quinoline-8-carboxylic acid azolide as set forth in claim 1.

10. A process for combatting the growth of unwanted plants, wherein the plants and/or the area to be kept free from unwanted plant growth are treated with a herbicidally effective amount of quinoline-8-carboxylic acid azolide as set forth in claim 2.

11. A compound of the formula I as set forth in claim 1, wherein A is 1,2,4-triazole, imidazole, 5-mercapto-1,2,4-triazole or 5-amino-1,2,4-triazole.

12. A process for combatting the growth of unwanted plants, wherein the plants and/or the area to be kept free from unwanted plant growth are treated with a herbicidally effective amount of a quinoline-8-carboxylic acid azolide as set forth in claim 11.

* * * * *